United States Patent
Booth

(10) Patent No.: US 7,144,403 B2
(45) Date of Patent: Dec. 5, 2006

(54) SURGICAL KNIFE

(75) Inventor: David E. Booth, Wyomissing Hills, PA (US)

(73) Assignee: Alcon, Inc., Hunenberg (CH)

( * ) Notice: Subject to any disclaimer, the term of this patent is extended or adjusted under 35 U.S.C. 154(b) by 699 days.

(21) Appl. No.: 10/629,404

(22) Filed: Jul. 29, 2003

(65) Prior Publication Data

US 2005/0033335 A1    Feb. 10, 2005

(51) Int. Cl.
*A61F 9/00* (2006.01)
*A61B 17/32* (2006.01)

(52) U.S. Cl. .......................................... 606/166; 30/355

(58) Field of Classification Search ................ 606/166, 606/167, 180, 185; 30/346.5, 353, 355, 357
See application file for complete search history.

(56) References Cited

U.S. PATENT DOCUMENTS

| | | | |
|---|---|---|---|
| 4,720,918 A | 1/1988 | Curry et al. | |
| 5,217,477 A * | 6/1993 | Lager | 606/167 |
| 5,713,915 A * | 2/1998 | Van Heugten et al. | 606/167 |
| 6,547,802 B1 * | 4/2003 | Nallakrishnan et al. | 606/166 |
| 6,554,840 B1 * | 4/2003 | Matsutani et al. | 606/107 |
| 6,613,061 B1 | 9/2003 | Olson et al. | |

FOREIGN PATENT DOCUMENTS

GB     2 130 955 A     6/1984

* cited by examiner

*Primary Examiner*—Vy Bui
(74) *Attorney, Agent, or Firm*—Jeffrey S. Schira

(57) ABSTRACT

A knife having a blade tip configuration that reduces incisional force by providing a more efficient distribution of tissue piercing and cutting forces over the cutting edges. The distal tip of the blade has a profile in plan view in the region of approximately 150 microns from the distal most point of the tip that may be described by the equation $w=ad^n$, where w is the distance from the blade's longitudinal axis to the blade's cutting edge, a is a constant of proportionality not greater than 0.5 and d is the distance along the blade's longitudinal axis from the extreme distal point of the blade tip. The extreme distal point of the tip has a slightly rounded, rather than pointy, profile, with a tip radius of approximately 40 microns or less.

11 Claims, 2 Drawing Sheets

SURGICAL KNIFE

BACKGROUND OF THE INVENTION

This invention relates generally to the field of surgical knives and, more particularly, to ophthalmic surgical knives.

A variety of surgical knives may be used during ophthalmic surgery to make or modify the opening incision into the globe. These knives are generally made from stainless steel or diamond. While steel knives can be used more than once, most steel knives are intended to be a single use disposable product. Diamond knives are designed to be a reusable item because diamond knives are expensive relative to steel knives. One of the benefits of diamond knife blades is that they can be honed very sharp, and the sharpness of diamond knives is generally superior to stainless steel knives. Manufacturers of prior art stainless steel knives have attempted to increase the sharpness of stainless steel knives by narrowing the distal blade tip, and making the extreme distal point of the blade very pointy. These narrow and pointy tips limit the blade's ability to distribute forces and makes these tips vulnerable to bending.

Accordingly, a need continues to exist for a stainless steel surgical knife having superior sharpness while resisting bending at the blade tip.

BRIEF SUMMARY OF THE INVENTION

The present invention improves upon the prior art by providing a knife having a blade tip configuration that reduces incisional force by providing a more efficient distribution of tissue piercing and cutting forces over the cutting edges. The distal tip of the blade has a profile in plan view in the region of approximately 150 microns from the distal most point of the tip that may be described by the equation $w=ad^n$, where w is the distance from the blade's longitudinal axis to the blade's cutting edge, a is a constant of proportionality no greater than 0.5 and d is the distance along the blade's longitudinal axis from the extreme distal point of the blade tip. The gradient or exponent, n, of the equation is between 0.9 and 1.4. The extreme distal point of the tip has a slightly rounded, rather than pointy, profile, with a tip radius of approximately 40 microns or less.

Accordingly, one objective of the present invention is to provide a knife having a distal tip point with a rounded profile.

Another objective of the present invention is to provide a knife having a profile in plan view in the region of approximately 150 microns from the distal most point of the tip that is described by the equation $w=ad^n$, where w is the distance from the blade's longitudinal axis to the blade's cutting edge, a is a constant of proportionality no greater than 0.5 and d is the distance along the blade's longitudinal axis from the extreme distal point of the blade tip.

Still another objective of the present invention is to provide a stainless steel surgical knife having superior sharpness while resisting bending These and other advantages and objectives of the present invention will become apparent from the detailed description and claims that follow.

DETAILED DESCRIPTION OF THE INVENTION

Figure 1:
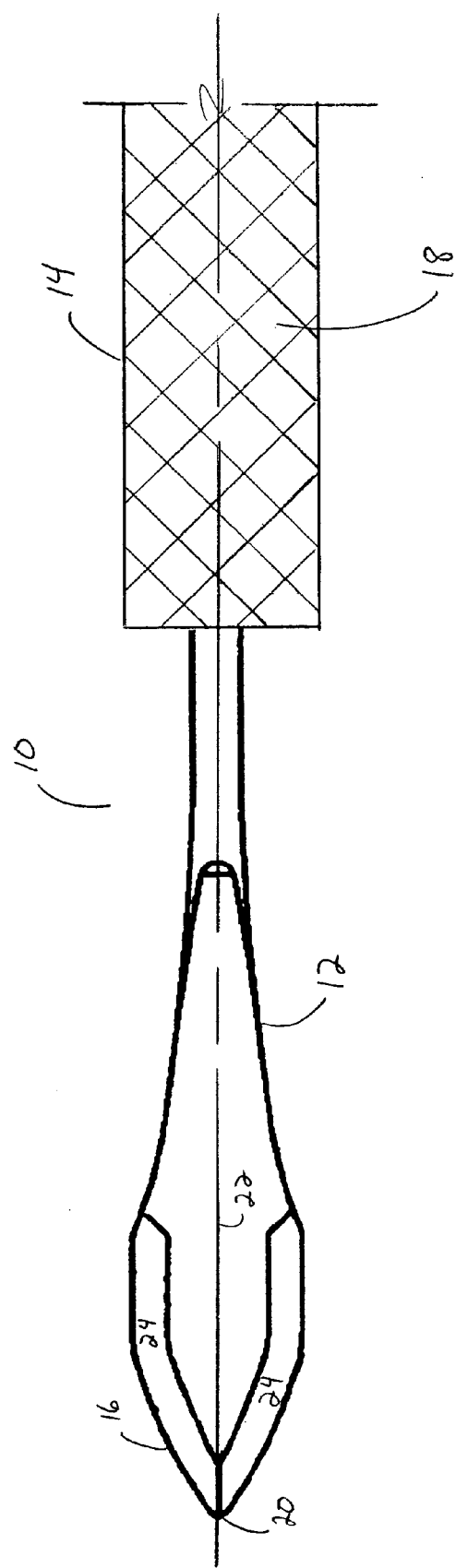
FIG. 1 is an enlarged partial plan view of the distal end of the surgical knife of the present invention.

As seen in FIG. 1, knife 10 of the present invention generally includes blade 12 and handle 14. Blade 12 may be any suitable surgical blade made, for example, from stainless steel, titanium, diamond or diamond-like coated substrate, such blades being well-known in the art, but is preferably made from grinding or coining wire stock stainless steel and sharpened by electropolishing techniques known in the art. Handle 14 preferably are made from injection-molded thermoplastic, but may also be made from other plastics, stainless-steel or titanium. Handle preferably contains ribs or knurling 18 to make handle 14 easier to grip. Blade 12 is attached to handle 14 by any suitable method, such as a press fit or adhesive.

Figure 2:
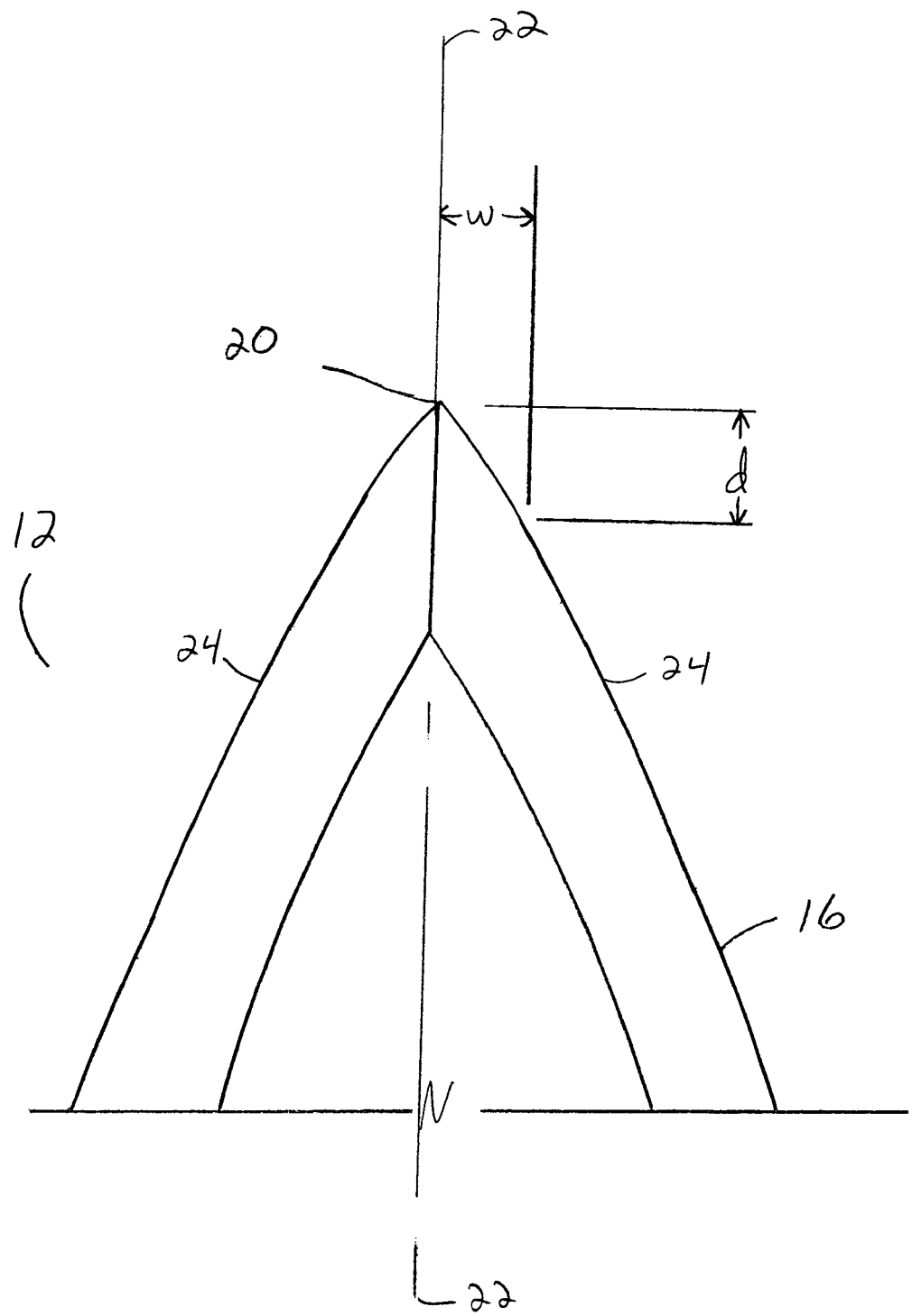
FIG. 2 is an enlarged partial plan view of the distal tip of the knife illustrated in FIG. 1.

As best seen in FIG. 2, blade 12 has a distal tip 16 having a distal point 20. Longitudinal centerline 22 extends longitudinally down the length of blade 12. Distal tip preferably has a thickness of approximately between 0.003 inches and 0.007 inches with an angle between cutting edges 24 of between approximately 12° and 20°. The inventor has discovered that the sharpness of blade 12, as measured by the force required to cause blade 12 to penetrate a sample tissue, varies according to the width (w) of blade 12 along a distance (d) down longitudinal axis 22 from distal point 20. The sharpness of blade 12 is optimized when the width of blade 12 generally follows the equation:

$$w=ad^n$$

for approximately the first 150 microns of distal tip 16 from distal point 20 where "a" is a constant of proportionality not greater than 0.5 and the gradient or exponent, "n", is between 0.9 and 1.4, derived by curve-fitting techniques or regression analysis well-known in the art.

Preferably, distal point 20 is slightly rounded, with a radius of 40 microns or less being preferred and a radius of between 10 microns and 40 microns being most preferred. Such a shape of distal tip 16 and distal point 20 on blade 12 distributes the tissue piercing and cutting forces over the blade edges more efficiently as the point of the blade enters and divides tissue.

Additionally, blade 12 may contain a lubricious or friction reducing coating, such as a fluorocarbon material, for example, PTFE (TEFLON®). Such a coating further reduces the force necessary to cause distal tip 16 to penetrate tissue.

This description is given for purposes of illustration and explanation. It will be apparent to those skilled in the relevant art that changes and modifications may be made to the invention described above without departing from its scope or spirit.

I claim:

1. A surgical knife, comprising:
   a) a handle;
   b) a blade having opposing cutting edges and a longitudinal axis, the blade being attached to the handle; and
   c) a distal tip on the blade, the distal tip having an extreme distal point,
   wherein the distal tip has a shape generally described by the equation $$w=ad^n$$

where
   w is the distance from the blade's longitudinal axis to the blade's cutting edges a is a constant of proportionality not greater than 0.5 n is an exponent approximately between 0.9 and 1.4 d is the distance along the blade's longitudinal axis from the extreme distal point of the blade tip.

2. The surgical knife of claim 1 wherein the distal tip has a thickness of approximately between 0.003 inches and 0.007 inches.

3. The surgical knife of claim 1 wherein an angle between the cutting edges is between approximately 12° and 20°.

4. The surgical knife of claim 1 wherein the distal point is slightly rounded, with a radius of less than approximately 40 microns.

5. The surgical knife of claim 4 wherein the radius is between approximately 10 microns and 40 microns.

6. The surgical knife of claim 1 wherein the blade contains a lubricious or friction reducing coating.

7. A surgical knife, comprising:
a) a handle;
b) a blade having opposing cutting edges and a longitudinal axis, the blade being attached to the handle and containing a lubricious or friction reducing coating; and
c) a distal tip on the blade, the distal tip having a slightly rounded end having an extreme distal point, wherein the distal tip has a shape generally described by the equation $$w = ad^n$$

where w is the distance from the blade's longitudinal axis to the blade's cutting edges a is a constant of proportionality not greater than 0.5 n is an exponent approximately between 0.9 and 1.4 d is the distance along the blade's longitudinal axis from the extreme distal point of the blade tip.

8. The surgical knife of claim 7 wherein the distal tip has a thickness of approximately between 0.003 inches and 0.007 inches.

9. The surgical knife of claim 7 wherein an angle between the cutting edges is between approximately 12° and 20°.

10. The surgical knife of claim 7 wherein the rounded end has a radius of less than approximately 40 microns.

11. The surgical knife of claim 10 wherein the radius is between approximately 10 microns and 40 microns.

* * * * *